(12) United States Patent
Jackson et al.

(10) Patent No.: US 11,944,728 B2
(45) Date of Patent: Apr. 2, 2024

(54) AIR TREATMENT DEVICE WITH SCENTED PAD MECHANISM

(71) Applicant: Helen of Troy Limited, St. Michael (BB)

(72) Inventors: Jeffrey Samuel Jackson, Sudbury, MA (US); Patrick Francis McDermott, Oxford, MA (US)

(73) Assignee: Helen of Troy Limited, St. Michael (BB)

( * ) Notice: Subject to any disclaimer, the term of this patent is extended or adjusted under 35 U.S.C. 154(b) by 666 days.

(21) Appl. No.: 17/179,497

(22) Filed: Feb. 19, 2021

(65) Prior Publication Data

US 2022/0265885 A1     Aug. 25, 2022

(51) Int. Cl.
    *A61L 9/03*                (2006.01)

(52) U.S. Cl.
    CPC .................. *A61L 9/03* (2013.01); *A61L 9/032* (2013.01); *A61L 2209/133* (2013.01); *A61L 2209/15* (2013.01)

(58) Field of Classification Search
    CPC ... A61L 9/03; A61L 9/032; A61L 9/12; A61L 9/122; A61L 2209/133; A61L 2209/15
See application file for complete search history.

(56) References Cited

U.S. PATENT DOCUMENTS

| | | | |
|---|---|---|---|
| 2,344,800 A | 3/1944 | Butcher | |
| 2,796,310 A | 6/1957 | Anderson | |
| 5,655,917 A | 8/1997 | Kaneshige et al. | |
| 7,494,172 B2 | 2/2009 | Herterich | |
| 7,643,734 B2 | 1/2010 | Wefler | |
| 8,544,766 B2 | 10/2013 | Webster | |
| 9,308,287 B2 | 4/2016 | Wolf | |
| 2012/0018529 A1 | 1/2012 | Gammon | |
| 2017/0067608 A1 | 3/2017 | Patton | |
| 2020/0268924 A1 | 8/2020 | Young | |

FOREIGN PATENT DOCUMENTS

CN            112618770         4/2021

OTHER PUBLICATIONS

International Search Report filed in PCT/US2022/015954 dated May 16, 2022.

*Primary Examiner* — Lessanework Seifu
(74) *Attorney, Agent, or Firm* — Rankin, Hill & Clark LLP

(57) ABSTRACT

An air treatment device includes a housing and a pad holder mounted within the housing. The pad holder has an opening providing access to a support surface for a scented pad. When positioned on the support surface the scented pad has a first end portion remote from the opening and a second end portion adjacent the opening. A mechanism associated with the pad holder is configured to at least partially remove the scented pad from the pad holder. The mechanism includes a lever arm and a pad pusher connected to the lever arm. The lever arm is configured such that movement of the lever arm pushes the pad pusher along the support surface toward the opening, the pad pusher engaging the first end portion of the scented pad and moving the second end portion of the scented pad at least partially out of the pad holder opening.

17 Claims, 7 Drawing Sheets

AIR TREATMENT DEVICE WITH SCENTED PAD MECHANISM

BACKGROUND

The ability to easily and efficiently control indoor environments is highly desirable. For this reason, a number of devices have been developed to control the temperature, humidity, odor and air quality of enclosed environments such as the rooms of a house. These air treatment devices include humidifiers, air purifiers, heaters, fans, scent masks, air fresheners and the like. For example, in temperate climates controlling humidity can be very important. During the winter and the months surrounding the winter, a lack of humidity in the air can cause significant discomfort to people. Humidifiers are a typical device used to control humidity. During these same months, many people develop colds and have sinus and chest congestion. One method for treating congestion and colds is by dispersing a soothing menthol scent into the air.

Humidifiers including means for generating a scent typically include an air freshener portion to disperse an aesthetic scent into the environment. Known humidifiers having an air freshening capability include humidifiers with scented objects disposed in an air path generated by a fan of the humidifier. The scented object continuously diffuses a scent into the air and the fan blows the scent into the surrounding environment. These scented objects known as "scented pads" typically are inserted into a slot or holder within the humidifier that is located adjacent to the fan and against a heated surface which releases the scented materials into the air. Mechanisms for removing the scented pad from the slot or holder are known; however, such mechanisms are not compact and can include multiple interconnected components.

BRIEF DESCRIPTION

According to one aspect, an air treatment device comprises a housing and a pad holder mounted within the housing. The pad holder has an opening providing access to a support surface for a scented pad. When positioned on the support surface the scented pad has a first end portion remote from the opening and a second end portion adjacent the opening. A mechanism associated with the pad holder is configured to at least partially remove the scented pad from the pad holder. The mechanism includes a lever arm and a pad pusher connected to the lever arm. The lever arm is configured such that movement of the lever arm pushes the pad pusher along the support surface toward the opening, the pad pusher engaging the first end portion of the scented pad and moving the second end portion of the scented pad at least partially out of the pad holder opening.

According to another aspect, an air treatment device comprises a pad holder having a support surface for a scented pad. A mechanism associated with the pad holder is configured to at least partially remove the scented pad from the pad holder. The mechanism includes a pushbutton, a lever arm connected to the pushbutton and a pad pusher connected to the lever arm. The pushbutton is supported by the pad holder for movement into the pad holder. The lever arm is configured such that movement of the pushbutton into the pad holder rotates the lever arm toward the pad pusher. The pusher pad is configured such that rotation of the lever arm moves the pad pusher along the support surface and into engagement with scented pad moving the scented pad at least partially out of the pad holder.

DETAILED DESCRIPTION

Figure 1:
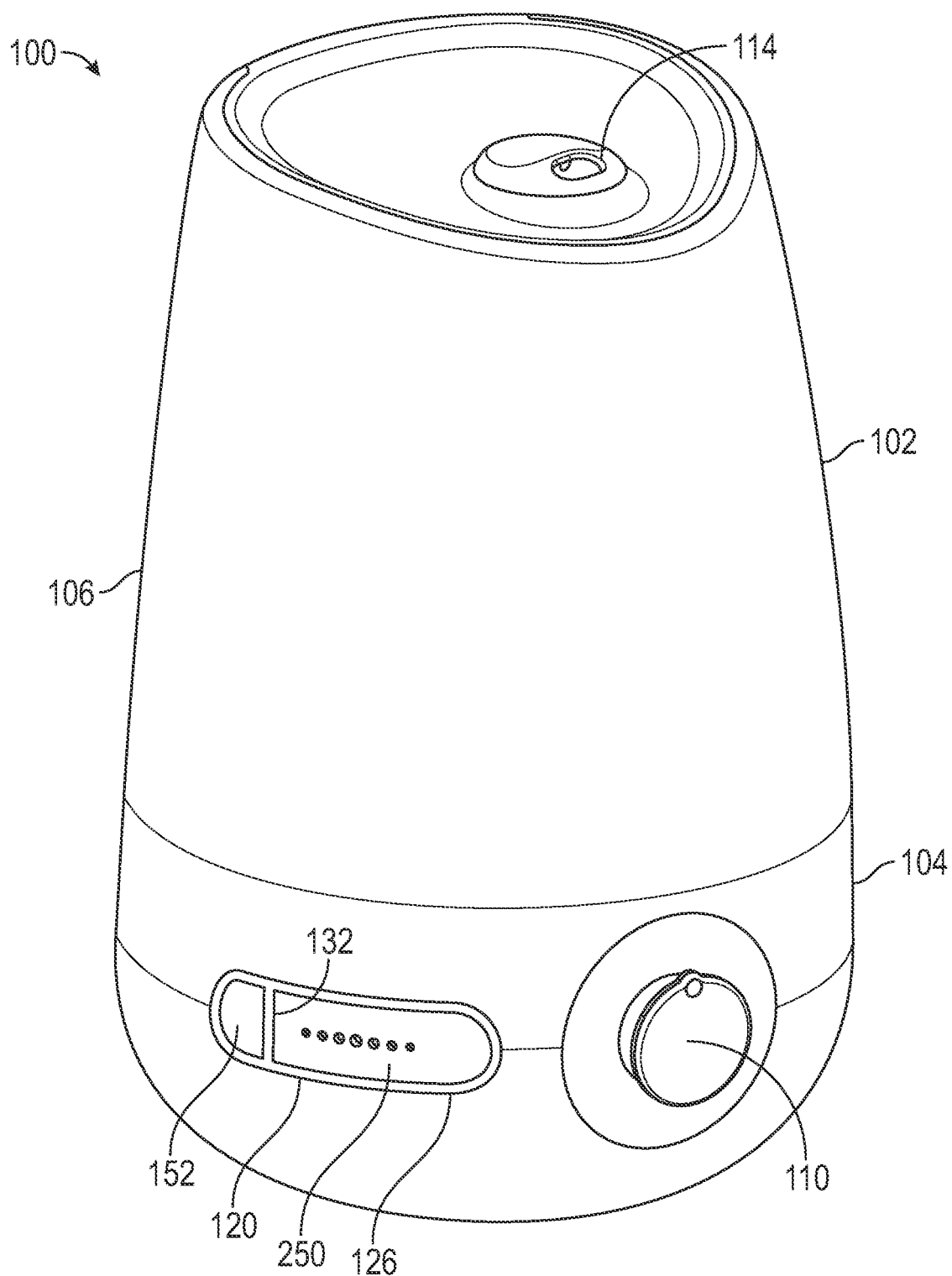
FIG. 1 is a perspective view of an air treatment device according the present disclosure, the air treatment device including a pad holder for a scented pad and a mechanism associated with the pad holder for removing the scented pad.

It should, of course, be understood that the description and drawings herein are merely illustrative and that various modifications and changes can be made in the structures disclosed without departing from the present disclosure. Referring now to the drawings, wherein like numerals refer to like parts throughout the several views, FIG. 1 illustrates an air treatment device or humidifier 100 having a housing 102 that is defined by a lower portion 104 and an upper portion 106 mounted atop the lower portion. The lower portion 104 preferably contains humidifying equipment, of any suitable type as known in the art, and a related humidifier control 110, such as a knob, a button or the like, to control the operation of the humidifying equipment. The upper portion 106 defines a water tank that is portable, and may be removed from the lower portion 104. The upper portion 106 includes a vent 114, and in operation of the humidifier 100, a flow of humidified air passes through a passage extended through the upper portion and the vent 114 to humidify the surrounding environment. In the case of a vaporizing humidifier, the flow may be steam.

Figure 2:
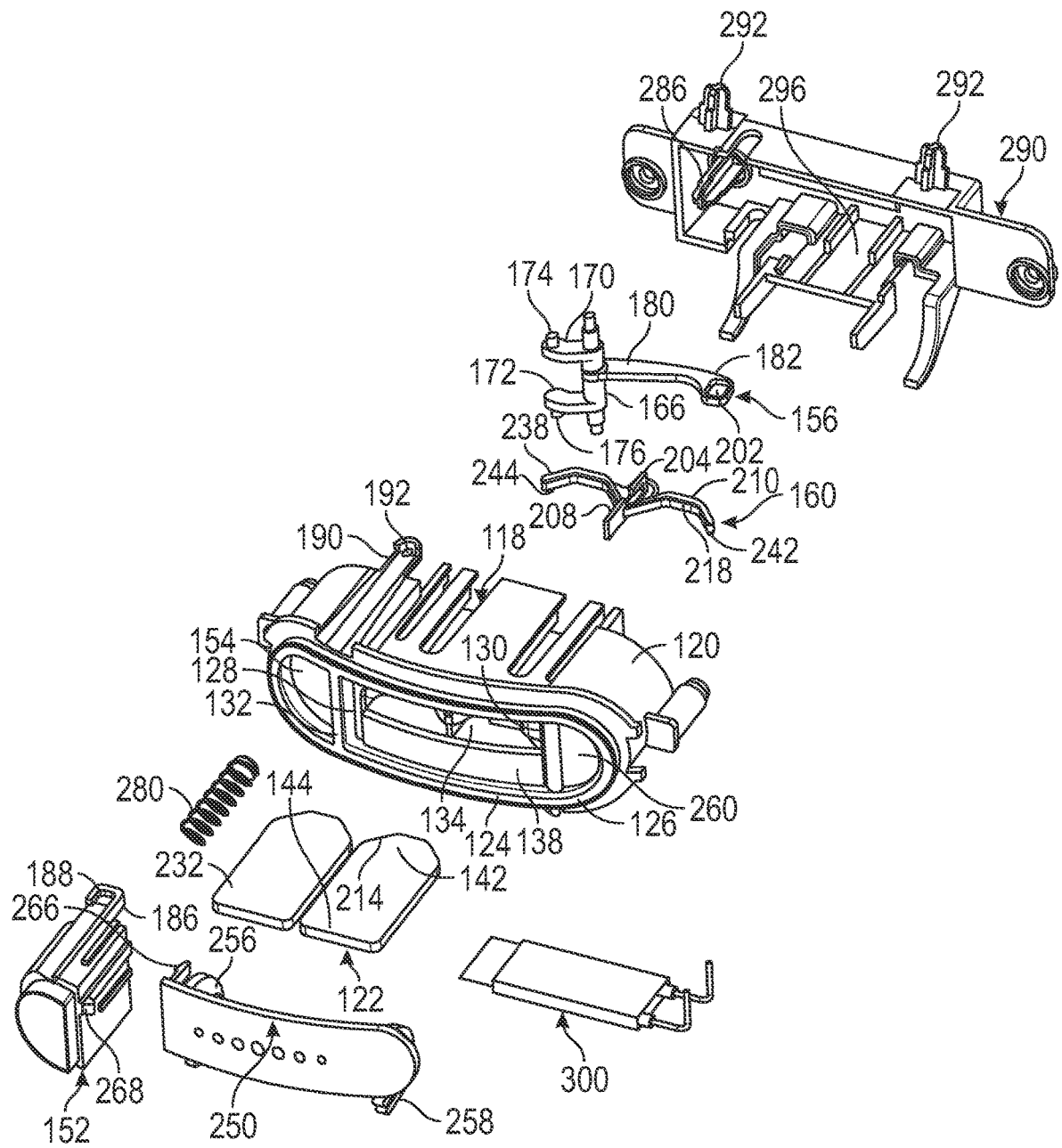
FIG. 2 is an exploded perspective view of the pad holder and the mechanism.
Figure 3:
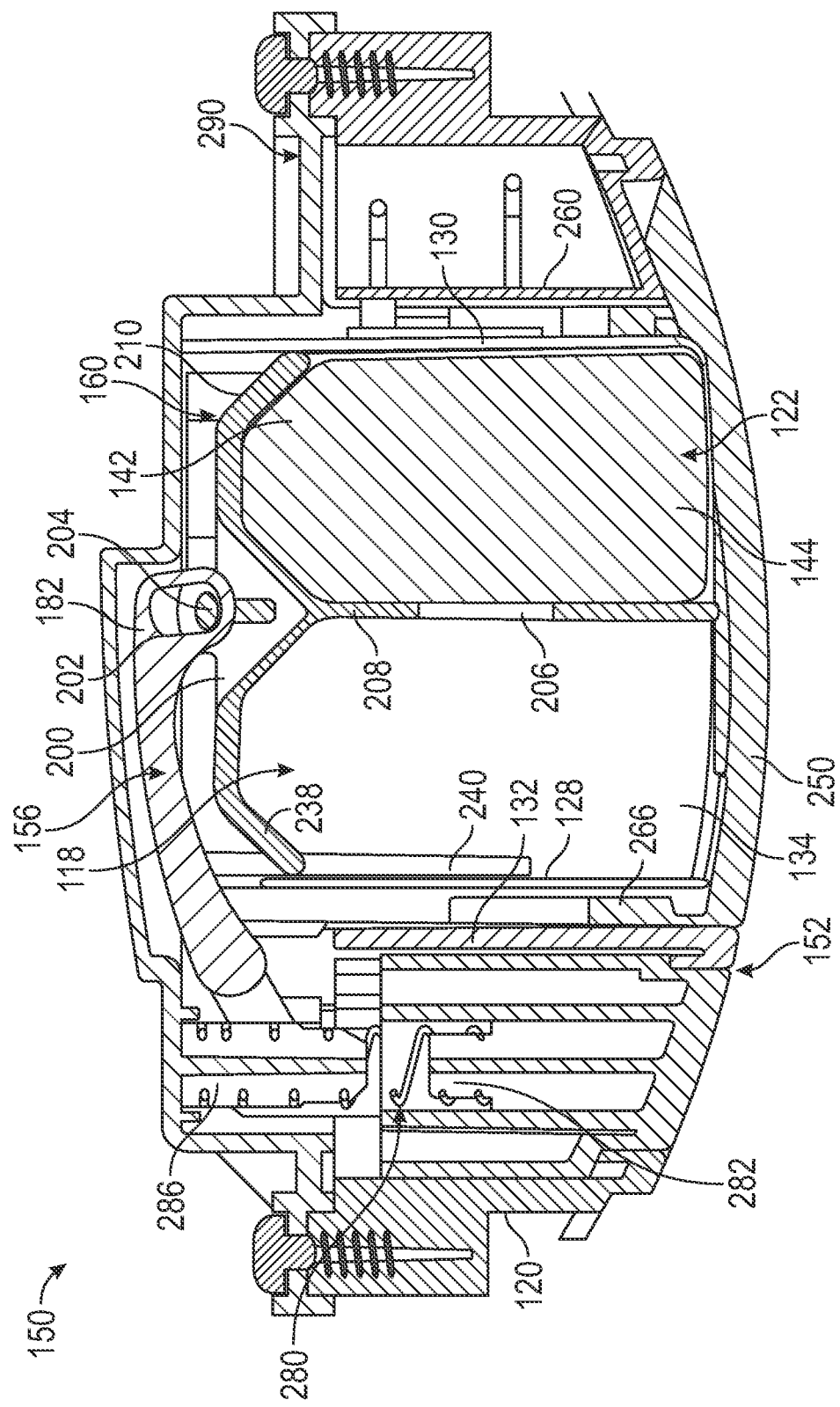
FIG. 3 is a cross-sectional view of the pad holder and the mechanism.

With additional reference to FIGS. 2 and 3, the humidifier 100 includes a pad holder 118 mounted within the housing 102, particularly the lower portion 104. The pad holder 118 includes a body 120 adapted for holding at least one scented pad 122. The body 120 defines an opening 124 at least partially framed by an outer periphery edge portion 126 and internal sidewalls 128, 130 of the pad holder 118. The opening 124 provides access to the at least one scented pad 122 selectively housed within the body 120. As shown, the edge portion 126 is intersected by a supporting wall 132 of the body 120 that extends substantially parallel to the internal sidewall 128, with the edge portion 126 and an outer face of the wall 132 both defining an exterior of the lower portion 104. The pad holder 118 further includes a support surface 134 for the at least one scented pad 122. The support surface 134 is extended rearward from a front wall 138 and is flanked by the internal sidewalls 128, 130. When fully positioned on the support surface 134 (FIG. 3), the at least one scented pad 122 has a first end portion 142 remote from the opening 124 and a second end portion 144 adjacent the opening.

The pad holder 118 further houses an exemplary mechanism 150 for removing the at least one scented pad 122 seated on the support surface 134 from the pad holder. In the depicted aspect, the mechanism 150 is actuated by an actuator 152 supported in a second opening 154 of the pad holder 118, the second opening defined by the body 120 and the supporting wall 132. It should be appreciated that the term "actuator" and variations thereof mean an element, device or mechanism, which is user operable to engage the mechanism 150. In the present aspect, the actuator 152 is a pushbutton moveable into the pad holder 118 and having an outer surface that defines the exterior of the lower portion 104. As will be described below, depressing the pushbutton 152 operates the mechanism 150 which, in turn, pushes the at least one scented pad 122 at least partially out of the opening 124 of the pad holder 118, allowing a user to easily remove the at least one scented pad from the humidifier 100. The mechanism 150 for removing the at least one scented pad 122 includes a lever arm 156 connected to the pushbutton 152 and a pad pusher 160 connected to the lever arm. The lever arm 156 is configured such that movement of the lever arm via the pushbutton 152 pushes the pad pusher 160 along the support surface 134 toward the opening 124, the pad pusher 160 engaging the first end portion 142 of the at least one scented pad 122 and moving the second end portion 144 of the scented pad at least partially out of the pad holder opening 124.

In FIG. 2, the lever arm 156 includes a post 166 with flanges 170, 172 projected from opposite end portions of the post. Each of the flanges 170, 172 includes a respective mounting pin 174, 176, which can be extended in opposite directions. An arm member 180 is extended from the post 166 in a direction substantially opposite the flanges 170, 172. A free end portion 182 of the arm member 180 is adapted to engage the pad pusher 160. The lever arm 156 is connected to the pad holder 118 via the post 166 and is also connected to the pushbutton 152 via the mounting pins 174, 176 provided on the flanges 170, 172. In the depicted aspect, the pushbutton 152 is provided with tabs having openings (only tab 186 with opening 188 is visible) sized to receive the mounting pins 174, 176. Similarly, the pad holder 118 is provided with tabs having openings (only tab 190 with opening 192 is visible) sized to receive the end positions of the post 166. With this arrangement the lever arm 156 is rotatably connected to the pad holder 118. Therefore, the lever arm 156 is configured such that movement of the pushbutton 152 into the pad holder 118 rotates the lever arm 156 relative to the pad holder 118 toward the pad pusher 160, causing sliding movement of the pad pusher 160 on the support surface 134. Therefore, because the mechanism 150 translates rotational movement of the lever arm 156 to sliding movement of the pad pusher 160, a compact layout of the mechanism in the pad holder 118 is achieved.

As shown in FIGS. 2 and 3, the pad pusher 160 includes a body 200 connected to the end portion 182 of the arm member 180. In the depicted aspect, the end portion 182 can be provided with an opening 202 sized to receive a finger 204 on the body 200. To support the sliding movement of the pad pusher 160, the support surface 134 defines at least one channel 206 (see FIG. 3) and the body 200 includes at least one guide 208 adapted to move through the at least one channel as the pad pusher moves along the support surface. Further, at least one arm 210 is extended from the body 200 for engaging the at least one scented pad 122. It should be appreciated that the at least one arm 210 is shaped to ensure that a particular shaped and sized scented pad is used with the humidifier 100. By way of example, the first end portion 142 of the at least one scented pad 122 can have a predetermined shape defined by, for example, at least one beveled edge 214, and the at least one arm 210 of the pad pusher 160 includes an engaging surface 218 shaped to mate with the first end portion. To further ensure the use of a proper scented pad, the pad holder 118 includes at least one rib 230 provided over the support surface 134, thereby limiting a thickness of the scented pad (see FIGS. 5 and 6) that can be received by the pad holder 118. The at least one rib 230 is sized to press the at least one scented pad 122 against the support surface 134. Therefore, the above arrangements prevent the use of a generic scented pad that is not optimized for the humidifier 100 which may result in inferior performance and damage to the humidifier.

In the depicted aspect, the at least one scented pad 122 is a first scented pad, and the support surface 134 is sized to support the first scented pad 122 together with a similarly shaped second scented pad 232. The at least one arm 210 of the pad pusher 160 is a first arm and the pad pusher includes a similarly shaped second arm 238 to engage the second scented pad 232. Therefore, the pad pusher 160 can simultaneously move the first scented pad 122 and the second scented pad 232 out of the pad holder opening 124. Further to this arrangement, the at least one channel 206 is a center channel separating the first and second scented pads 122, 232 on the support surface 134. The support surface 134 can be provided with outboard channels adjacent the internal sidewalls 128, 130 (only outboard channel 240 adjacent internal sidewall 128 is shown in FIG. 3) that receive guide pins 242, 244 provided on the respective arms 210, 238 of the pad pusher 160. In addition, the at least one rib 230 is a first rib for pressing the first scented pad 122 and the pad holder 118 includes a second rib 248 for pressing the second scented pad 232 against the support surface 134.

With reference to FIGS. 2-6, an outer door 250 is connected to the pad holder 118 and is movable between a closed position for closing the opening 124 of the pad holder and an open position providing access to the at least one scented pad 122. The door 250 is provided with mounting hooks 256, 258 shaped to engage the body 120 of the pad holder 118 and allow for movement of the door 250 about that engagement with the body 120. As shown, the mounting hook 256 is received between the internal sidewall 128 and the supporting wall 132, and the mounting hook 258 is received between the internal sidewall 130 and an additional supporting wall 260 of the body 120, which extends substantially parallel to the internal sidewall 130. The door 250 further includes a locking arm 266 adapted to releasably engage one of the supporting wall 132 of the pad holder body 120 and the pushbutton 152 to maintain the door in the closed position. In the depicted aspect, the locking arm 266 extends through an opening in the supporting wall 132 and is releasably engaged to the pushbutton 152. And the pushbutton 152 is configured such that movement of the pushbutton into the pad holder 118 disengages the locking arm 266 from the pushbutton 152 causing the door 250 to move to the open position. By way of example, in FIG. 2 the pushbutton 152 includes a barb 268 correspondingly shaped to engage the locking arm 266 and move the locking arm away from the pushbutton 152 and the supporting wall 132, allowing the door 250 to open.

Further depicted in FIGS. 2 and 3, a biasing member, such as a spring 280, is provided to outwardly bias the pushbutton 152 from within the second opening 154. The spring 280 has one end portion mounted on a post 282 of the pushbutton and an opposite end portion mounted on a post 286 of a rear cover part 290. The rear cover part 290 is fastened to the pad holder 118 and can include mounting posts 292 for attaching the entire assembly of FIG. 2 within the lower portion 104 of the humidifier 100. The rear cover part 290 includes a base wall 296 which can support a heating element 300. The heating element 300 is electrically activated and positioned beneath the support surface 134, such that heating element 300 warms each scented pad 122, 232 during operation. As the temperature of each scented pad 122, 232 rises scent is dispersed into the air. In the shown aspect, the heating element 300 is a positive temperature coefficient (PTC) element; however, the heating element may be formed of a heating coil or the like.

In use, a user depresses the pushbutton 152 to move the door 250 to the open position so that at least one of the scented pads 122, 232 can be inserted into the pad holder 118. The scented pad 122, 232 is placed on the support surface 134 and is pressed against the support surface via the rib 230, 248. According to the depicted aspect of FIG. 6, an inner surface 308 of the door 250 can be provided with a rib portion 310 adapted to further seat the scented pad 122, 232 into the pad holder as the door is moved back to the closed position.

Figure 4:
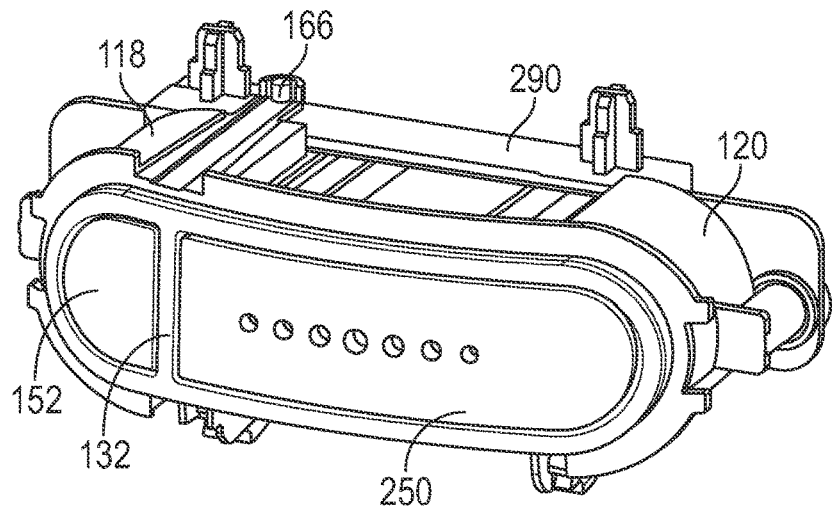
FIGS. 4, 5 and 6 are perspective views of the pad holder and the mechanism showing removal of the scented pad from the pad holder.
Figure 5:
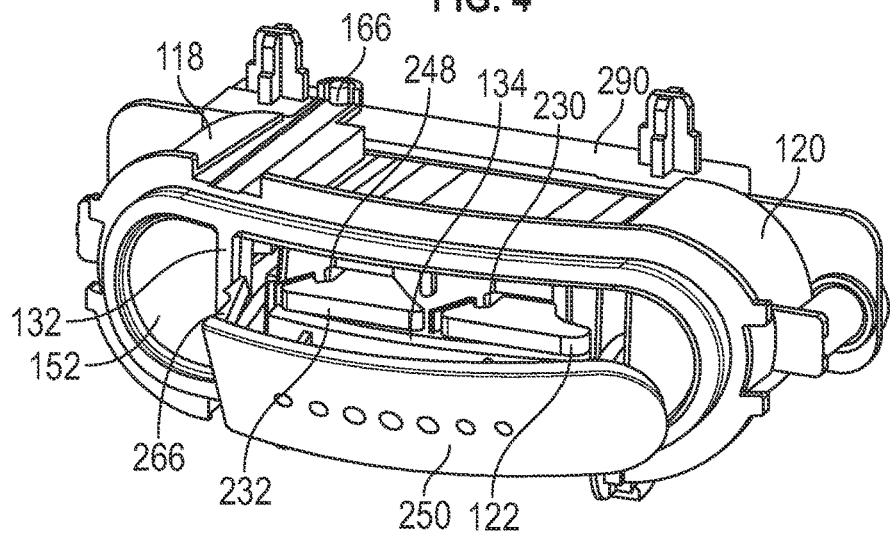
Figure 6:
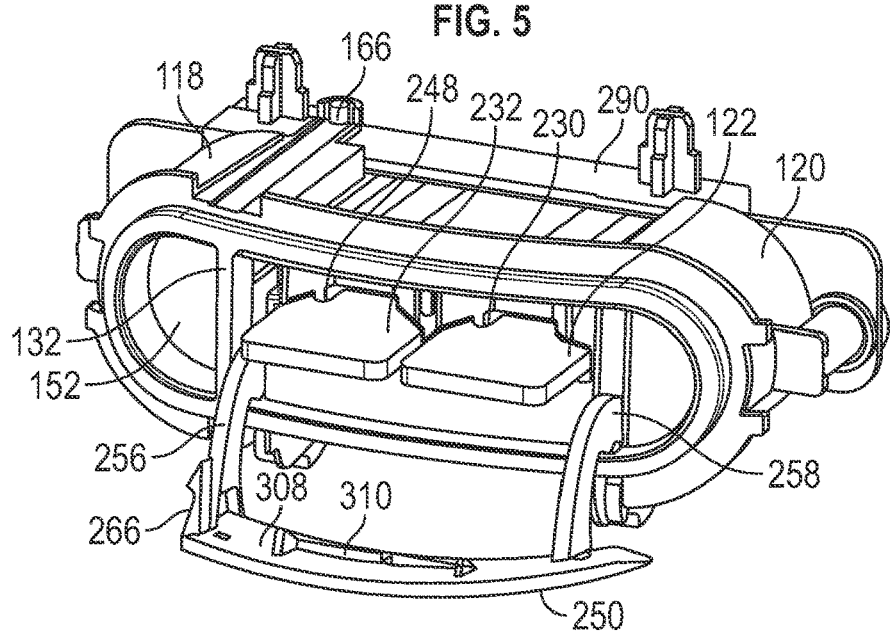
Figure 7:
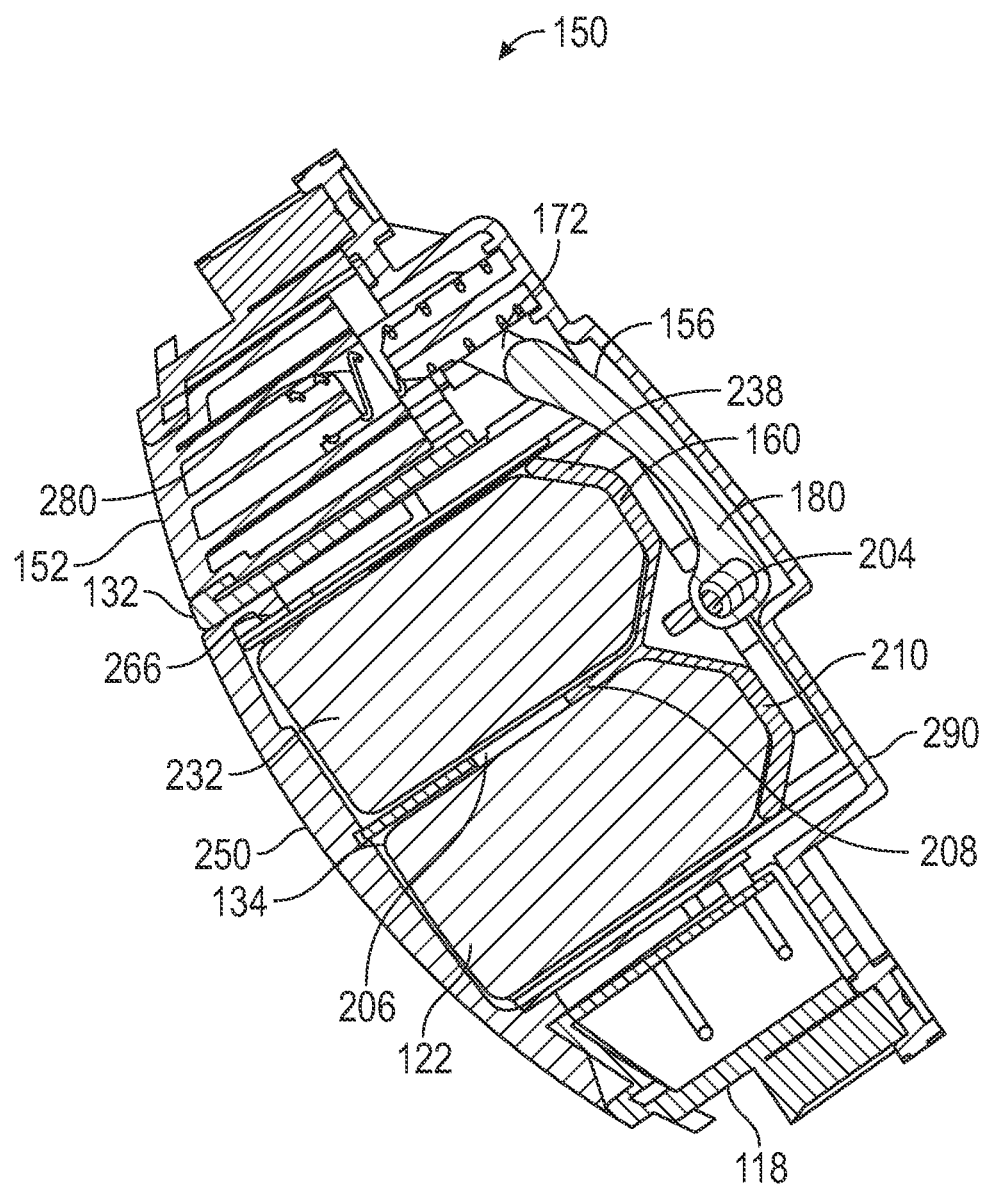
FIGS. 7, 8 and 9 are respective cross-sectional views of FIGS. 4, 5 and 6.
Figure 8:
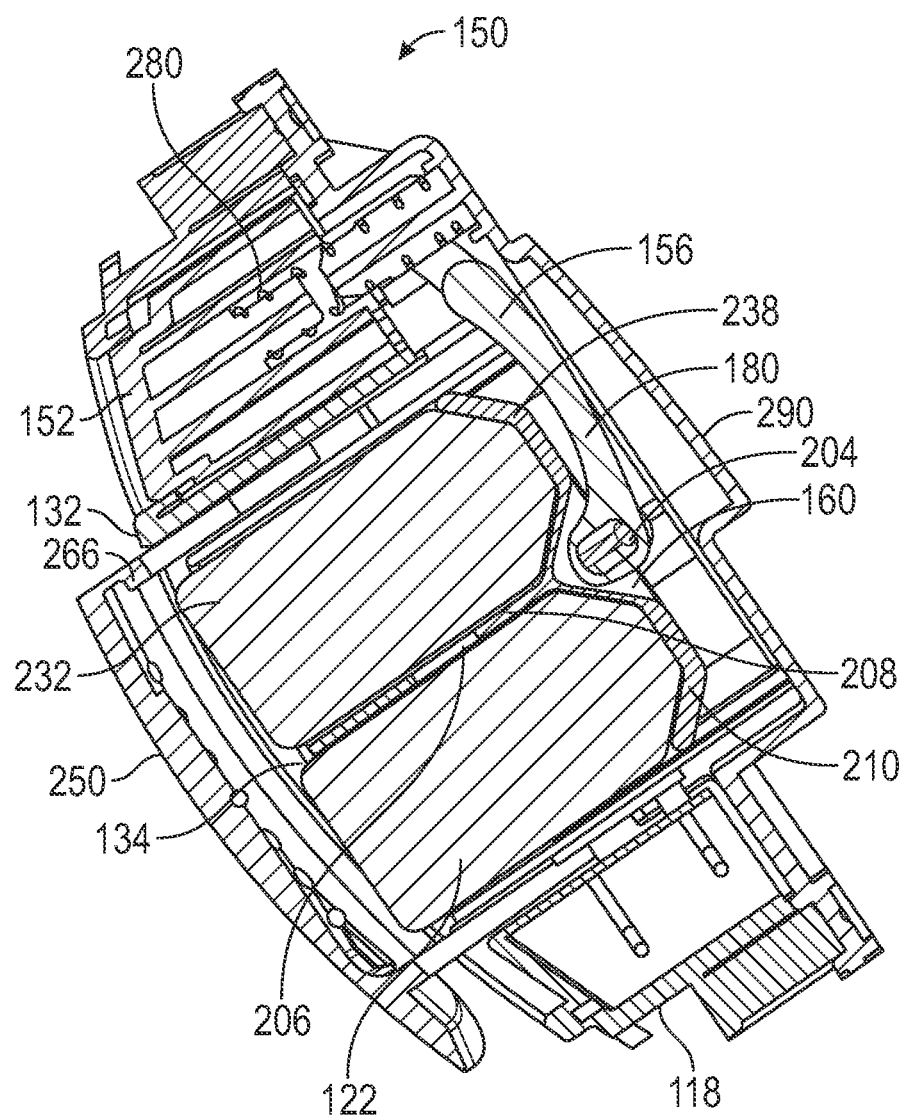
Figure 9:
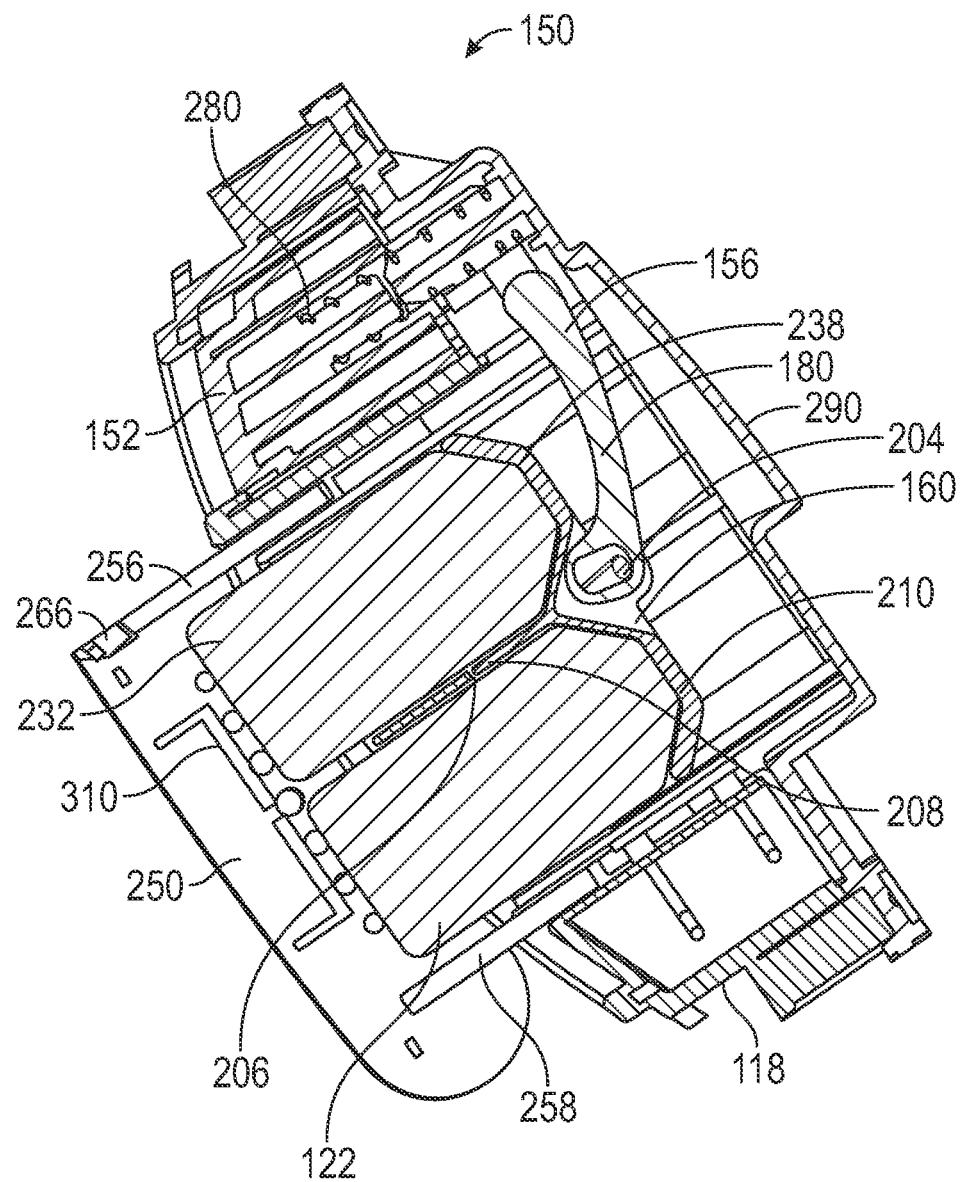

FIG. 4-9 illustrate operation of the mechanism 150 for removing the scented pad 122, 232. In FIGS. 4 and 7, the door 250 is in the closed position with the door locking arm 266 engaged to the pushbutton 152. The pushbutton 152 is in its outwardly biased position via the spring 280, and with the pushbutton 152 connected to the flanges 170, 172 as described above (only a portion of flange 172 is visible in FIG. 7), the arm member 180 of the lever arm 156 and the pad pusher 160 are located adjacent to the rear cover part 290. The scented pad 122, 232 abuts against the arm 210, 238 of the pad pusher, and the guide 208 of the pad pusher 160 is located at a rear of the channel 206 formed in the support surface 134. In FIGS. 5 and 8, the pushbutton 152 is partially depressed, which disengaged the locking arm 266 of the door 250 from the pushbutton 152, allowing the door to move partially to its open position. Depressing the pushbutton 152 rotates the arm member 180 of the lever arm 156 into engagement with the pad pusher 160. The pad pusher is caused to slide along the support surface 134, guided by the guide 208 within the channel 206, with the arm 210, 238 pushing the scented pad 122, 232. In FIGS. 6 and 9, the door 250 is in the open condition and the pushbutton 152 is fully depressed. The arm member 180 of the lever arm 156 is fully rotated and the pad pusher 160 is moved to a position where the guide 208 is located at a front of the channel 206. The scented pad 122, 232 is pushed at least partially out of the pad holder 118 via the arm 210, 238 allowing the user to grasp and completely remove the scented pad. It should be appreciated that the pushbutton 152 is biased back to position in FIG. 4 via the spring 280, and as the pushbutton is returned the lever arm 156 and the pad pusher 160 are moved back to their initial positions in FIG. 7. A replacement scented pad can then be placed into the pad holder 118 and the door 250 can then be moved back to the closed position, where the locking arm 266 is again engaged to the pushbutton 152.

It should be appreciated that the scented pads 122, 232 described herein can be made from a porous material that may include wood, cotton or synthetic fibers and can include oil or alcohol based scent ingredients, which when heated releases a scent into the atmosphere. It should also be noted that although the description herein describes the exemplary mechanism 150 for removing the scented pads as being a part of the depicted humidifier 100, it can be appreciated by one of ordinary skill in the art that certain aspects of the present invention can be used in conjunction with other air treatment devices such as a heater, air purifier or a fan for example.

It will be appreciated that the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. An air treatment device comprising:
   a housing;
   a pad holder mounted within the housing, the pad holder having an opening providing access to a support surface for a scented pad, when positioned on the support surface the scented pad having a first end portion remote from the opening and a second end portion adjacent the opening; and
   a mechanism associated with the pad holder and configured to at least partially remove the scented pad from the pad holder, the mechanism including a lever arm and a pad pusher connected to the lever arm, wherein the lever arm is configured such that movement of the lever arm pushes the pad pusher along the support surface toward the opening, the pad pusher engaging the first end portion of the scented pad and moving the second end portion of the scented pad at least partially out of the pad holder opening.

2. The device of claim 1, wherein the mechanism includes an actuator supported by the pad holder and connected to the lever arm, the actuator having an outer surface that defines an exterior of the device.

3. The device of claim 2, wherein the actuator is a pushbutton that is movable into the pad holder, and the lever arm is configured such that movement of the pushbutton into the pad holder rotates the lever arm toward the pad pusher.

4. The device of claim 3, wherein the lever arm is rotatably connected to the pad holder.

5. The device of claim 3, including a door movable between a closed position for closing the opening of the pad holder and an open position providing access to the scented pad, the door including a locking arm engaging the pushbutton in the closed position and the pushbutton is configured such that movement of the pushbutton into the pad holder disengages the locking arm from the pushbutton causing the door to move to the open position.

6. The device of claim 5, wherein an inner surface of the door includes a rib portion adapted to seat the scented pad into the pad holder.

7. The device of claim 1, wherein the support surface defines at least one channel and the pad pusher includes at least one guide adapted to move through the at least one channel as the pad pusher moves along the support surface.

8. The device of claim 1, wherein the pad holder includes at least one rib provided over the support surface, the at least one rib sized to press the scented pad against the support surface.

9. The device of claim 1, wherein the first end portion of the scented pad has a predetermined shape defined by at least one beveled edge and the pad pusher includes an engaging surface shaped to mate with the first end portion.

10. The device of claim 1, including a heating element supported by the pad holder beneath the support surface.

11. The device of claim 1, wherein the air treatment device is one of a humidifier, a heater, a fan, and an air purifier.

12. An air treatment device comprising:
    a pad holder having a support surface for a scented pad; and a mechanism associated with the pad holder and configured to at least partially remove the scented pad from the pad holder, the mechanism including a pushbutton, a lever arm connected to the pushbutton and a pad pusher connected to the lever arm, wherein the pushbutton is supported by the pad holder for movement into the pad holder, the lever arm is configured such that movement of the pushbutton into the pad holder rotates the lever arm toward the pad pusher, wherein the pad pusher is configured such that rotation of the lever arm moves the pad pusher along the support surface and into engagement with scented pad moving the scented pad at least partially out of the pad holder.

13. The device of claim 12, wherein the lever arm is rotatably connected to the pad holder.

14. The device of claim 12, wherein the support surface defines at least one channel and the pad pusher includes at least one guide adapted to move through the at least one channel as the pad pusher moves along the support surface.

15. The device of claim 12, including a door movable between a closed position for closing an opening of the pad holder and an open position providing access to the scented pad, the door including a locking arm engaging one of the pad holder and the pushbutton in the closed position and the pushbutton is configured such that movement of the pushbutton into the pad holder disengages the locking arm causing the door to move to the open position.

16. The device of claim 12, wherein the pad holder includes at least one rib provided over the support surface, the at least one rib sized to press the scented pad against the support surface.

17. The device of claim 12, wherein the support surface is sized to support the scented pad and a second scented pad, and the pad pusher includes a first and second arms to engage the scented pad and the second scented pad and simultaneously move the scented pad and the second scented pad out of the pad holder.

* * * * *